United States Patent
Kume et al.

(10) Patent No.: US 6,326,517 B1
(45) Date of Patent: Dec. 4, 2001

(54) METHOD OF PRODUCING BENZAMIDES

(75) Inventors: Takashi Kume; Michio Ishida; Satoru Narizuka, all of Saitama; Yuzuru Morino, Yamaguchi; Makoto Koide, Saitama, all of (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 09/458,079

(22) Filed: Dec. 10, 1999

(30) Foreign Application Priority Data

Dec. 10, 1998 (JP) .................................................. 10-351528
Dec. 24, 1998 (JP) .................................................. 10-366804

(51) Int. Cl.$^7$ ........................ C07C 231/00; C07C 233/00
(52) U.S. Cl. ........................................... 564/132; 564/183
(58) Field of Search ..................................... 564/132, 183

(56) References Cited

U.S. PATENT DOCUMENTS 3,825,594  7/1974  Houlihan .

OTHER PUBLICATIONS

Lukmanov, V.G., Alekseeva, L.A., Burmakov, A.I., and Yagupolskii, L.M. (1973) "Fluorination of Aromatic Carboxylic Acids by Sulfur Tetrafluoride. VIII. Synthesis of Vicinal Poly (trifluoromethyl)–benzenes". *Zh. Org. Khim.* 9 (5) :1019–24. An English abstract of this document is attached (Chemical Abstracts vol. 79:42101).

Schoenberg, A. and Heck, R.F. (1974) "Palladium–Catalyzed Amidation of Aryl, Heterocyclic, and Vinylic Halides". *J. Org. Chem.* 39:3327–31.

*Primary Examiner*—Sreeni Padmanabhan
*Assistant Examiner*—J. Parsa
(74) *Attorney, Agent, or Firm*—Crowell & Moring LLP

(57) ABSTRACT

A method of producing benzamides represented by the following general formula (1):

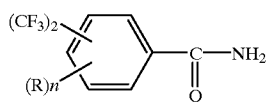

(1)

where R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or a alkoxycarbonyl group having 2 to 5 carbon atoms; and n is 0 or an integer ranging from 1 to 3. The method comprises the step of allowing an aromatic compound represented by the following general formula (2) to react with carbon monoxide and ammonia in the presence of a metal of the group VIII of the periodic table and phosphine:

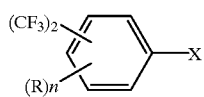

(2)

where X is halogen (fluorine, chlorine, bromine or iodine), trifluoromethanesulfonate group, alkylsulfonate group having 1 to 4 carbon atoms, or substituted or unsubstituted arylsulfonate group; R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or alkoxycarbonyl group having 2 to 5 carbon atoms; and n is 0 or an integer ranging from 1 to 3.

21 Claims, No Drawings

METHOD OF PRODUCING BENZAMIDES

BACKGROUND OF THE INVENTION

1. Field of the Invention

This invention relates to improvements in a method of producing benzamides which are useful for intermediate products of medicines and agricultural chemicals.

2. Description of the Prior Art

Hitherto, benzamides have been able to be produced by reacting ammonia or ammonium salt with benzoic halides, benzoic anhydrides or benzoic acids.

U.S. Pat. No. 3,825,594 discloses a production method for aryl halide having two trifluoromethyl groups in an aryl ring, in which 2,6- or 2,4-bis(trifluoromethyl) benzoic acids are formed into acid chlorides which are subjected to amidation with primary amines. Additionally, a literature (Chemical Abstracts, Vol. 79: 42101, Zh. Org. Khim. 1973, 9(5), 1019–24 (Russ)) discloses that 2,6-bis(carboxytrifluoro methyl) benzene is reacted with $SF_4$ to produce 2,6-bis (trifluoromethyl) benzoylfluoride which is then reached with ammonia thereby to form 2,6-bistrifluoromethyl benzoic amides. Further, a literature (J. Org. Chem., Vol. 39, No. 23, 1974, 3327–3331) discloses that aryl halides, carbon monoxide and primary or secondary amine are reacted in the presence of a catalytic amount of triphenylphosphine-palladium salt complex thereby to produce corresponding secondary and tertiary amides.

As discussed above, trifluoromethyl benzamides can be produced from acid chloride or acid fluoride of bistrifluoromethyl benzoic acid. However, difficulties have been encountered in the above conventional techniques. That is, the conventional techniques require to prepare the acid chloride or the acid fluoride as a precursor. As a result, a production process of the trifluoromethyl benzamides requires multi-state reaction steps.

SUMMARY OF THE INVENTION

It is an object of the present invention to provide an improved production method of benzamides, which can effectively overcome difficulties encountered in conventional production methods for benzamides.

Another object of the present invention is to provide an improved production method of benzamides, which can provide benzamides at a single reaction step from aromatic compounds which are readily available.

A further object of the present invention is to provide an improved production method of benzamides, which can provide bis(trifluoromethyl) benzamides at a single reaction step from aromatic halides which are readily available.

A still further object of the present invention is to provide an improved production method of benzamides, which can provide benzamides at a single reaction step from aromatic compounds, while largely reducing an amount of expensive noble metal catalysts such as palladium to be consumed in reaction of the production method.

A first aspect of the present invention resides in a method of producing benzamides represented by the following general formula (1):

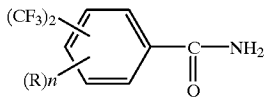

(1)

where R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or a alkoxycarbonyl group having 2 to 5 carbon atoms; and n is 0 or an integer ranging from 1 to 3.

The method comprises the step of allowing an aromatic compound represented by the following general formula (2) to react with carbon monoxide and ammonia in the presence of a metal of the group VIII of the periodic table and phosphine:

(2)

where X is halogen (fluorine, chlorine, bromine or iodine), trifluoromethanesulfonate group, alkylsulfonate group having 1 to 4 carbon atoms, or substituted or unsubstituted arylsulfonate group; R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or alkoxycarbonyl group having 2 to 5 carbon atoms; and n is 0 or an integer ranging from 1 to 3.

According to the first aspect, the benzamides can be produced at a single reaction from aromatic compound (preferably aromatic halide) having bis(trifluoromethyl) group, carbon monoxide and ammonia, thereby simplifying the process of production of the benzamides.

A second aspect of the present invention resides in a method of producing benzamides, comprising the following steps:

(a) allowing an aromatic compound represented by the following general formula (2) to react with carbon monoxide and ammonia in the presence of palladium and phosphine in a reaction system:

(2)

where X is halogen (fluorine, chlorine, bromine or iodine), trifluoromethanesulfonate group, alkylsulfonate group having 1 to 4 carbon atoms, or substituted or unsubstituted arylsulfonate group; R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or a alkoxycarbonyl group having 2 to 5 carbon atoms; and n is 0 or an integer ranging from 1 to 3, (b) separating at least benzamide represented by the following general formula (1):

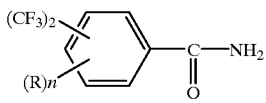

where R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or a alkoxycarbonyl group having 2 to 5 carbon atoms; and n is 0 or an integer ranging from 1 to 3; and (c) adding the aromatic compound represented by the general formula (2), ammonia and carbon monoxide into the reaction system from which at least the benzamide is separated, so as to accomplish reaction in the reaction system.

According to the second aspect, the benzamides can be produced at a single reaction from aromatic compound (preferably aromatic halide) having bis(trifluoromethyl) group, carbon monoxide and ammonia, while sharply reducing the amount of expensive catalyst to be used in the reaction.

A third aspect of the present invention resides in a method of producing benzamides, comprising the following steps:

(a) allowing an aromatic compound represented by the following general formula (2) to react with carbon monoxide and ammonia in the presence of palladium and phosphine in a reaction system:

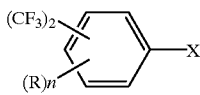

where X is halogen (fluorine, chlorine, bromine or iodine), trifluoromethanesulfonate group, alkylsulfonate group having 1 to 4 carbon atoms, or substituted or unsubstituted arylsulfonate group; R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or a alkoxycarbonyl group having 2 to 5 carbon atoms; and n is 0 or an integer ranging from 1 to 3, (b) separating at least benzamide represented by the following general formula (1):

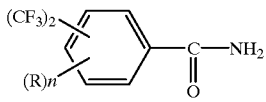

where R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or a alkoxycarbonyl group having 2 to 5 carbon atoms; and n is 0 or an integer ranging from 1 to 3; and (d) recovering palladium-phosphine complex compound from the reaction system; and (e) using the palladium-phosphine complex compound recovered in the step (d) as a catalyst.

Other aspects of the present invention will become apparent from the description made hereinafter.

DETAILED DESCRIPTION OF THE INVENTION

According to an aspect of the present invention, a method of producing benzamides represented by the following general formula (1) is provided:

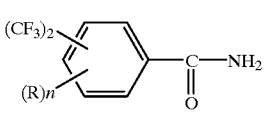

where R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or a alkoxycarbonyl group having 2 to 5 carbon atoms; and n is 0 or an integer ranging from 1 to 3.

The method comprises the step of allowing an aromatic compound represented by the following general formula (2) to react with carbon monoxide and ammonia in the presence of a metal of the group VIII of the periodic table and phosphine:

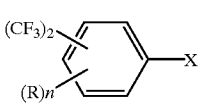

where X is halogen (fluorine, chlorine, bromine or iodine), trifluoromethanesulfonate group, alkylsulfonate group having 1 to 4 carbon atoms, or substituted or unsubstituted arylsulfonate group; R is trifluoromethyl group, trifluoromethyloxy group, halogen (fluorine, chlorine, bromine or iodine), nitro group, acetyl group, cyano group, alkyl group having 1 to 4 carbon atoms, aLkoxy group having 1 to 4 carbon atoms, or alkoxycarbonyl group having 2 to 5 carbon atoms; and n is 0 or an integer ranging from 1 to 3.

The aromatic compound represented by the general formula (2) is is composed of halogen; trifluoromethanesulfonate group, alkylsulfonate group having 1 to 4 carbon atoms, or substituted or unsubstituted arylsulfonate group and aryl group having at least two trifluoromethyl groups. It is practically preferable to use the compound in the form of halide, from the viewpoint of being readily available. The halogen represented by X is fluorine, chlorine, bromine or iodine, in which bromine or iodine is preferable. R is preferably chlorine, bromine or iodine from the viewpoint of usability of the resultant benzamides as intermediate products in a fluorochemical field.

Concerning R, examples of the alkyl group having 1 to 4 carbon atoms are methyl group, ethyl group, n-propyl group, and i-propyl group. Examples of the alkoxy group having 1 to 4 carbon atoms are niethoxy group, ethoxy group, n-propoxy group, and i-propoxy group. Examples of alkoxycarbonyl group having 2 to 5 carbon atoms are methoxycarbonyl group, ethoxycarbonyl group, n-propoxycarbonyl group, and i-propoxycarbonyl group.

As the aromatic compound represented by the general formula (2), halogeno-bis(trifluoromethyl) benzene represented by the following general formula (3) is preferable:

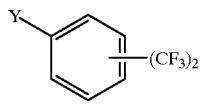

(3)

where Y is bromine or iodine.

The aromatic compound (having only two trifluoromethyl groups) represented by the general formula (3) is not limited to particular ones, in which examples of the aromatic compound are 1-bromo-2,4-bis(trifluoromethyl)benzene, 1-iodo-2,4-bis(trifluoromethyl)benzene, 1-bromo-3,5-bis(trifluoromethyl)benzene [3,5-bis(trifluoromethyl)bromobenzene], 1-iodo-3,5-bis(trifluoromethyl)benzene [3,5-bis(trifluoromethyl)iodobenzene], 2-bromo-1,3-bis(trifluoromethyl)benzene, 2-iodo-1,3-bis(trifluoromethyl) benzene, 2-bromo-1,4-bis(trifluoromethyl)benzene, 2-iodo-1,4-bis(trifluoromethyl)benzene, 4-bromo-1,2-bis(trifluoromethyl)benzene, and the like.

The aromatic compound (having substituted group other than two fluoromethyl groups) represented by the general formula (2) is also suitable for the production method of the present invention. Examples of such aromatic compound are 1-bromo-2,3,4-tris(trifluoromethyl)benzene, 1-bromo-2,4,5-tris(trifluoromethyl)benzene, 1-iodo-2,3,5-tris(trifluoromethyl)benzene, 1-iodo-2,4,5-tris(trifluoromethyl)benzene, 2-bromo-1,3,5-tris(trifluoromethyl)benzene, 5-bromo-1,2,3-tris(trifluoromethyl)benzene, 5-iodo-1,2,3-tris(trifluoromethyl)benzene, 2-iodo-1,3,4,5-tetrakis(trifluoromethyl)benzene, 1,2-dibromo- 3,4,5,-tris(trifluoromethyl)benzene, and the like; 1,3-dichloro-5-iodo-2,4-bis(trifluoromethyl)benzene, 1,2-dibromo-4,5-bis(trifluoromethyl)benzene, 1,4-dibromo-2,5-bis(trifluoromethyl)benzene, 1-bromo-2-chloro-3,5-bis(trifluoromethyl)benzene [2-chloro-3,5-bis(trifluoromethyl)bromobenzene],1-bromo-2-methoxy-3,5-bis(trifluoromethyl)benzene, 1-iodo-2-methoxy-3,5-bis(trifluoromethyl)benzene, 2-bromo-1-iodo-3,5-bis(trifluoromethyl)benzene, 2-bromo-1-nitro-3,5-bis(trifluoromethyl)benzene, 2-bromo-3,4-dichloro-1,5-bis(trifluoromethyl)benzene, 5-bromo-2-chloro-1,3-bis(trifluoromethyl)benzene, and the like. It will be understood that the aromatic compound having the substituted group and represented by the formula (2) is not limited to the above examples.

It is very preferable from the viewpoint of high usability of the resultant product to use as starting material 3,5-bis(trifluoromethyl)bromobenzene or 3,5-bis(trifluoromethyl)iodobenzene, and the corresponding compound halogenated on benzene nucleus, such as 2-chloro-3,5-bis(trifluoromethyl)bromobenzene. In this regard, if the former two bromobenzene and iodobenzene are used as the starting material in the production method of the present invention, 3,5-bis(trifluoromethyl)benzamide is obtained. If the latter bromobenzene is used as the starting material, 2-chloro-3, 5-bis(trifluoromethyl)benzamide is obtained.

When the aromatic compound represented by the general formula (2) is used in the production method of the present invention, only halogen combined to the aromatic (aryl) ring is converted into carbamoyl group to form a product, in which no change is made on the substituent represented by R. In a compound having a plurality of different halogens in the aryl ring, it is general that the halogens are preferentially reactive in the order of iodine, bromine, chlorine and fluorine; however, the order may change according to the location of the substituent (R) in the aryl ring and the kinds of the substituent (R).

Next, the production method of the benzamides represented by the general formula (1) will be discussed in detail.

The amount of ammonia used in the production method is not less than 1 mole, preferably 1 to 10 moles, more preferably 2 to 5 moles, relative to 1 mol of the aromatic compound represented by the general formula (2). If the used amount of the ammonia is less than 1 mole, reaction cannot be completed. Even if the used amount of the ammonia exceeds 10 moles, no problem arises from the viewpoint of yield in reaction; however, it becomes excessive and uneconomical.

Carbon monoxide used in the production method is preferably in the state of pure gas, in which it is unnecessary to have a high purity. Accordingly, carbon monoxide gas may be used in a state of being diluted or mixed with an inert gas such as nitrogen gas, argon gas, carbon dioxide gas. The amount of carbon monoxide used in the production method is not less than 1 mole relative to 1 mole of the aromatic compound represented by the general formula (2). The pressure of carbon monoxide used in the production method is not lower than ordinary or atmospheric pressure and not higher than 150 kg/cm$^2$, preferably not higher than 50 kg/cm$^2$.

Examples of the metal of the group VIII of the periodic table to be used in the production method are metals in the state of element, such as iron, cobalt, palladium, platinum, rhodium, ruthenium, iridium, osmium, and the like. The metal can be used as element and otherwise used in a state of being carried on a carrier such as graphite, silica gel, alumina, silica-alumina, molecular sieve and the like. Palladium of the above-listed metals is particularly preferable. The above-listed metals may be used in the form of a metallic salt or compound and therefore used as acetate, carbonate, nitrate, chloride, bromide, or the like. Concrete examples of the metallic salt of the metal are palladium acetate, palladium chloride, cobalt acetate, cobalt carbonate, cobalt chloride, ruthenium bromide, and the like.

The metal of the group VIII of the periodic table may be used in the form of metal complex, Phosphine is preferable as a ligand of the metal complex. Examples of phosphines are represented by the following general formula:

(4)

where $R^1$ independently represents lower alkyl group, phenyl group, or phenyl group substituted with lower alkyl group; and

(5)

where $R^1$ independently represents lower alkyl group; and Q is a bivalent group. Here, Q is alkylene group represented by $-(CH_2)_m-$ where m is an integer ranging from 2 to 8. The above-mentioned lower alkyl group preferably has 1 to 4 carbon atoms. Concrete examples of such phosphine are triphenylphosphine, tri-o-tolyl phosphine, tri-m-tolyl phosphine, tri-p-tolyl phosphine, 1,1'-bis(diphenylphosphino)ferrocene, 1,4-bis(diphenylphosphino)butane, 1,3-bis(diphenylphosphino)propane, 1,2-bis(diphenylphosphino)ethane, tri-n-butylphosphine, triethylphosphine, and the like. Acetonitrile, benzonitrile, carbon monoxide and the like are exemplified as other ligands. Of the above-listed compounds, the phosphines are preferable in which the phosphines having phenyl group and phenyl group substituted with the lower alkyl group are more preferable.

Concrete examples of the metal complex are $PdCl_2[P(o-Me-Ph)_3]_2$, $PdCl_2[P(m-Me-Ph)_3]_2$, $PdCl_2[P(p-Me-Ph)_3]_2$, $PdCl_2(PMe_3)_2$, $PdCl_2(PPh_3)_2$, $PdBr_2(PPh_3)_2$, $Pd(PPh_3)_4$, $PdCl_2[P(Ph)_2CH_2CH_2P(Ph)_2]$, $PdCl_2[P(Ph)_2CH_2CH_2CH_2CH_2P(Ph)_2]$, $PdCl_2(PhCN)_2$, $Pd(CO)(PPh_3)_3$, $PhPdI(PPh_3)_2$, $PhPdBr(PPh_3)_2$, $PhPdBr(PMePh_2)_2$, $PdCl_2(PMePh_2)_2$, $PdCl_2(PEt_2Ph)_2$, $PdCl_2(PMe_2Ph)_2$, $Pd_2Br_4(PPh_3)_2$, $PdCl_2(PtEt_3)_2$, $PdCl_2(bpy)_2$, $RhCl(PPh_3)_3$, $RhCl(CO)(PPh_3)_2$, $Pt(CO)_2(PPh_3)_2$, $H_4Ru(CO)_{12}$, $RU_3(CO)_{12}$, $CoCl(PPh_3)_3$, $CoH(N_2)(PPh_3)_3$, $CoCl_2(PEtPh_2)_2$, $HCo(CO)_4$, $Co_2(CO)_8$, and the like, in which Me is methyl group; Et is ethyl group; and Ph is phenyl group.

In general, it is not apparent as to which intermediate state and which activated condition a catalyst takes in the reaction system. However, in view of the fact the present invention is intended to produce an objective product, it will be understood that the form of metallic compound, the ligand and the metal complex is not limited to particular ones as far as the metal, the ligand and reagents participated in the reaction are in such a combination as to exhibit activity under the reaction condition of the production method.

The amount of the ligand to be used in the reaction system may be more than a value required to form the metal complex upon reaction of the ligand and the metal. For example, upon such adjustment of 2 moles of triphenylphosphine relative to 1 mole of palladium, triphenylphosphine and palladium are added into the reaction system. However, the adjustment may be made such that not less than 2 moles of triphenylphosphine is relative to 1 mole of palladium. The metal and ligand are added independently or in the form of complex into the reaction system. The amount of the metal of the group VIII of the periodic table to be used in the production method is within a range of from 0.00001 to 0.5 mole, preferably 0.00005 to 0.1 mole, more preferably 0.0001 to 0.05 mole, relative to 1 mole of the aromatic compound represented by the general formula (2). If the amount of the metal is not more than 0.00001 mole, proceeding of the reaction is retarded and therefore not practical. If the amount of the metal is more than 0.5 mole, no problem will arise from the viewpoint of reaction; however, economical disadvantages are provided.

The reaction of the production method of the present invention can be carried out without using organic solvent, or using organic solvent. The aromatic compound represented by the general formula (2) may be used as both substrate and the organic solvent. Additionally, other examples of the organic solvent are ethers such as diethyl ether, diethyleneglycoldimethyl ether, tetrahydrofuran, dioxane and the like; aromatic hydrocarbons such as benzene, toluene, xylene, nitrobenzene, chlorobenzene, and the like; nitrites such as acetonitrile, benzonitrile; N,N-dimethylacetoamide; N,N-dimethylformamide; N-methylpyrrolidone; dimethyl sulfoxide; hexamethylphosphoramide and the like. Additionally, water may be used in place of the organic solvent. The above-listed substances (solvents) are used singly or in combination (in the form of a mixture containing at least two substances). The amount of the solvent is not limited to a particular value from the viewpoint of reaction; however, using an excessive amount of the solvent requires a large-sized reaction apparatus and therefore is not preferable.

It is preferable that water is present in the reaction system for the reasons set forth below. That is, since ammonia is high in vapor pressure, a high pressure is, in general, required to increase the concentration of ammonia in a reaction system containing only organic solvent. However, the solubility of ammonia to water is high, and therefore presence of water accomplishes a remarkable pressure lowering in the reaction system. Additionally, salt produced as a result of the reaction can be readily transferred to the layer of water. This contributes to promotion of the reaction, while facilitating a purification operation. In case that water is used as the solvent, it is preferable to use in combination a solvent which can suitably dissolve benzamide produced in the reaction system. As this solvent, each one of the above-listed solvents can be used. The reaction may be promoted by adding into the reaction system a phase transfer catalyst such as quaternary ammonium salt and crown ether. The amount of water to be used is not limited to particular values; however, it is preferable to use such an amount of water that a first layer mainly containing water and a second layer mainly containing organic solvent are formed in the reaction system. A reaction temperature in the reaction system is within a range of from 10 to 200° C., preferably 10 to 150° C. A reaction time in the reaction system is within a range of from 0.1 to 30 hours, preferably 0.5 to 10 hours.

The reaction of the production method is preferably carried out in a pressure container (reactor) formed of a corrosion-resistant material such as glass, stainless steel, platinum, fluorine-contained resin. Prior to carrying out the reaction, the pressure container is charged with the aromatic compound represented by the general formula (2), the metal of the group VIII of the periodic table and the phosphine serving as the catalyst, ammonia, and the organic solvent and/or water if necessary, in their predetermined amount. At this time, in case of using water, ammonia is charged in the form of ammonia water, which is preferable. In case of using no water, ammonia is charged in the form of gas or liquid. Then, gas inside the reactor is substituted with carbon monoxide so as to set the pressure of carbon monoxide at a predetermined level. Thereafter, heating the reactor is started. When the inside temperature of the reactor reaches a predetermined level (for example, not lower than 50° C., preferably about 80° C.), the inside pressure of the reactor is adjusted at a predetermined level. Thereafter, the inside temperature and pressure are adjusted at predetermined levels or programmed conditions while controlling the flow amount of carbon monoxide to be introduced into the reactor.

The following examples are included merely to aid in the understanding of the invention, and variations may be made on the examples by one skilled in the art without departing from the spirit and scope of the invention. It will be understood that "pressure" used in the examples is indicated as gage pressure.

EXAMPLE 1

A 500-ml autoclave made of stainless steel was charged with 200 g of 3,5-bis(trifluoromethyl)broniobenzene, 100 ml of tetrahydrofuran, 0.763 g of palladium acetate, 1.79 g of triphenylphosphine, and 185 g of 25% ammonia water. Stirring for the content of the autoclave was started, upon which nitrogen gas displacement for the autoclave was made three times, and carbon monoxide gas displacement for the autoclave was made three times. Thereafter, the initial pressure of carbon monoxide gas was set at 4 kg/cm², and then heating for the autoclave was started. After lapse of 1 hour, the inside temperature of the autoclave reached 100° C., at which the inside pressure of the autoclave was adjusted at 10 kg/cm². Thereafter, the inside temperature and pressure were respectively kept at 100° C. and 10 kg/cm², while adjusting the introduction amount of carbon monoxide gas.

After lapse of 8 hours, the heating of the autoclave was stopped to cool the inside of the autoclave, and the gas inside the autoclave was purged. A reaction mixture or liquid was taken out into a separatory funnel, in which the reaction liquid was separated into two (upper and lower) layers. The lower layer (organic layer) was sampled and condensed by an evaporator. Subsequently, n-hexane was added to the condensed organic layer. Then, the condensed upper layer was subjected to suction filtration to filtrate precipitated crystals thereby obtaining 127.4 g of 3,5-bis(trifluoromethyl)benzamide crystal having a melting point ranging from 160 to 162° C.

EXAMPLE 2

A 1000-ml autoclave made of stainless steel was charged with 350 g of 3,5-bis(trifluoromethyl)bromobenzene, 233 ml of tetrahydrofuran, 1.34 g of palladium acetate, 1.34 g of 1,4-bis(diphenylphosphino)butane (dppb), 325 g of 25% ammonia water. Stirring for the content of the autoclave was started, upon which nitrogen gas displacement for the autoclave was made three times, and carbon monoxide gas displacement for the autoclave was made three times. Thereafter, the initial pressure of carbon monoxide gas was set at 4 kg/cm$^2$, and then heating for the autoclave was started. After lapse of 1 hour, the inside temperature of the autoclave reached 85° C., at which the inside pressure of the autoclave was adjusted at 8 kg/cm$^2$. During reaction, the inside temperature and pressure were respectively kept at 85° C. and 8 kg/cm$^2$.

After lapse of 7 hours, the autoclave was cooled, and the gas inside the autoclave was purged. A reaction mixture or liquid was taken out into a separatory funnel, in which the reaction liquid was separated into two (upper and lower) layers. The lower layer (organic layer) was sampled. Extraction was made on the upper layer (water layer) by using ethyl acetate to obtain an extract. The extract was mixed with the above organic layer to obtain a mixture. The mixture was dried over magnesium sulfate and subjected to suction filtration to obtain a filtrate. The filtrate was condensed by using an evaporator. n-Hexane was added to the condensed filtrate. Then, the condensed filtrate was subjected to suction filtration so as to filtrate precipitated crystals, thereby obtaining 101.3 g of 3,5-bis(trifluoromethyl)benzamide.

EXAMPLE 3

A 500-ml autoclave made of stainless steel was charged with 200 g of 3,5-bis(trifluoromethyl)bromobenzene, 200 ml of N,N-dimethylformamide (DMF), 0.763 g of palladium acetate, 3.57 g of triphenylphosphine, and 139 g of 25% ammonia water. Stirring for the content of the autoclave was started, upon which nitrogen gas displacement for the autoclave was made three times, and carbon monoxide gas displacement for the autoclave was made three times. Thereafter, the initial pressure of carbon monoxide gas was set at 4 kg/cm$^2$, and then heating for the autoclave was started. After lapse of 1 hour, the inside temperature of the autoclave reached 100° C., at which the inside pressure of the autoclave was adjusted at 10 kg/cm$^2$. During reaction, the inside temperature and pressure were respectively kept at 100° C. and 10 kg/cm$^2$.

After lapse of 4.5 hours, the autoclave was cooled, and the gas inside the autoclave was purged. A reaction mixture or liquid was subjected to suction filtration so as to obtain a filtrate. Thereafter, 200 g of ice and 200 ml of ethyl acetate were added to the filtrate. The filtrate was then transferred into a separatory funnel thereby separating an organic layer from an aqueous layer. Extraction was made two times on the aqueous layer by using ethyl acetate so as to obtain an extract. The extract was added to the organic layer to obtain a mixture. The mixture was dried over magnesium sulfate anhydride and then subjected to suction filtration to obtain a filtrate. The filtrate was concentrated by using an evaporator. A mixture solvent of n-hexane and ethyl acetate was added to the concentrated filtrate to allow crystals to be precipitated. The precipitated crystals were filtered thereby to obtain 62.2 g of 3,5-bis(trifluoromethyl)benzamide.

EXAMPLE 4

A 500-ml autoclave made of stainless steel was charged with 13.33 g of 2-chloro-3,5-bis(trifluoromethyl)bromobenzene, 5.93 g of tetrahydrofuran, 24.6 mg of PdCl$_2$ (dppb), 34.7 mg of dppb, and 9.57 g of 29% of ammonia water. Stirring for the content of the autoclave was started, upon which nitrogen gas displacement for the autoclave was made three times, and carbon monoxide gas displacement for the autoclave was made three times. Thereafter, the initial pressure of carbon monoxide gas was set at 2.6 kg/cm$^2$, and then heating for the autoclave was started. After lapse of 1 hour, the inside temperature of the autoclave reached 100° C., at which the inside pressure of the autoclave was adjusted at 10 kg/cm$^2$. Thereafter, the inside temperature was kept at 100 to 105° C. while the inside pressure was kept at 10 kg/cm$^2$, controlling the introduction amount of carbon monoxide gas.

After lapse of 6 hours, the heating of the autoclave was stopped to cool the inside of the autoclave, and the gas inside the autoclave was purged. 5N hydrochloric acid was added to a reaction mixture or liquid in the autoclave in such a manner as to adjust pH at a value of not higher than 1. Thereafter, 0.5 ml of diethyl ether was added to the reaction liquid to extract organic components which were in an ether layer. This ether layer was subjected to a gas chromatograph analysis. As a result, it was confirmed that objective 2-chloro-3,5-bis(trifluoromethyl)benzamide was produced in a yield of 13.4%. The gas chromatograph analysis provided a mass spectrum date (for 2-chloro-3,5-bis(trifluoromethyl) benzamide) of 291;293 (intensity ratio 10:3, parent peak), 275;277 (intensity ratio 10:3), 247;249 (intensity ratio 10:3), 212.

EXAMPLE 5

A 100-ml autoclave made of stainless steel was charged with 13.3 g of 3,5-bis(trifluoromethyl)iodobenzene, 5.9 g of tetrahydrofuran, 26.4 mg of palladium acetate, 61.7 mg of triphenylphosphine, and 9.2 g of 29% ammonia water. Stirring for the content of the autoclave was started, upon which nitrogen gas displacement for the autoclave was made three times, and carbon monoxide gas displacement for the autoclave was made three times. Thereafter, the initial pressure of carbon monoxide gas was set at 2.6 kg/cm$^2$, and then heating for the autoclave was started. After lapse of 1 hour, the inside temperature of the autoclave reached 100° C., at which the inside pressure of the autoclave was adjusted at 10 kg/cm$^2$. Thereafter, the inside temperature and pressure were respectively kept at 105° C. and 10 kg/cm$^2$, while adjusting the introduction amount of carbon monoxide gas.

After lapse of 6 hours, the heating of the autoclave was stopped to cool the inside of the autoclave. A reaction mixture or liquid in the autoclave was treated in the same manner as that in Example 4 to obtain an ether layer similar that in Example 4. The ether layer was subjected to the gas chromatograph analysis. As a result, it was confirmed that objective 3,5-bis(trifluoromethyl)benzamide was produced in a yield of 29.1%.

Hereinafter, another aspect of the present invention will be discussed.

A method of producing benzamides, comprises the following steps:

(a) allowing an aromatic compound represented by the following general formula (2) to react with carbon monoxide and ammonia in the presence of palladium and phosphine in a reaction system:

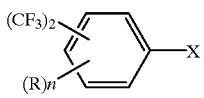

(2)

where X is halogen (fluorine, chlorine, bromine or iodine), trifluoromethanesulfonate group, alkylsulfonate group having 1 to 4 carbon atoms, or substituted or unsubstituted arylsulfonate group; R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or a alkoxycarbonyl group having 2 to 5 carbon atoms; and n is 0 or an integer ranging from 1 to 3, (b) separating at least benzamide represented by the following general formula (1):

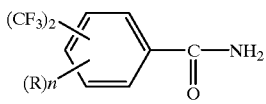

(1)

where R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or a alkoxycarbonyl group having 2 to 5 carbon atoms; and n is 0 or an integer ranging from 1 to 3; and (c) adding said aromatic compound represented by the general formula (2), ammonia and carbon monoxide into the reaction system from which at least said benzamide is separated, so as to accomplish reaction in the reaction system.

The above steps (c) may be replaced with the following two steps (d) and (e):

(d) recovering palladium-phosphine complex compound from the reaction system; and (e) using the palladium-phosphine complex compound recovered in the step (d) as a catalyst.

At the second step (b) of the production method, at least benzamide represented by the following general formula (1) is separated and taken out:

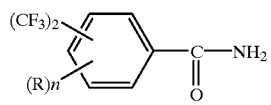

(1)

where R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or a alkoxycarbonyl group having 2 to 5 carbon atoms; and n is 0 or an integer ranging from 1 to 3.

When the reaction rate of the aromatic compound as a raw material in a reaction mixture or liquid reaches a desired level, introduction of carbon monoxide is stopped to cool the reactor. After gas inside the reactor is purged, the reaction liquid is taken out. In case of using ammonia water or water as the solvent, the reaction liquid is formed into two layers, in which the objective reaction product is contained in the organic layer. Crude objective reaction product is obtained by distilling out the solvent and removing the catalyst. This reaction product or composition can be purified by a conventional method.

At the third step (c) of the production method, reaction raw materials such as the aromatic compound represented by the general formula (2), ammonia and carbon monoxide are added into the reaction system from which at least the benzamide is separated, so as to accomplish reaction in the reaction system. More specifically, the reaction raw materials are supplied into the reaction system from which the objective product and necessarily produced by-product in the step (a) has been removed, without newly supplying palladium and phosphine. At this time, the reaction conditions at the step (c) is to be similar to that at the step (a); however, it is not required to be identical with that at the step (a) and therefore may be suitably changed. At the step (c), palladium and/or phosphine may be supplementarily added; however, they are not necessarily required.

At the fourth step (d) of the production step, palladium-phosphine complex compound is recovered from the reaction mixture containing the product, the solvent and the like obtained by the reaction at the first step (a). It is not apparent as to which state palladium in the reaction system is taking; however, it is assumed that complex compound containing palladium and phosphine is formed. It is not necessary that the complex compound existing in the reaction system and the palladium-phosphine complex compound obtained at the step (d) are the same substance; however, they are readily convertible therebetween under circumstances similar to the reaction system.

Examples of the palladium-phosphine complex compound are one represented by the following general formula (10):

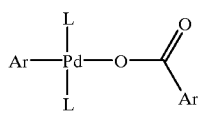

(10)

where Ar is aryl group, and L is phosphine represented by the general formula (4) or (5); and one represented by the following general formula (11):

Ar—PdL$_2$X (11)

where Ar is aryl group; X is halogen (fluorine, chlorine, bromine or iodine), trifluoromethanesulfonate group, alkylsulfonate group having 1 to 4 carbon atoms, or substituted or unsubstituted arylsulfonate group; and L is phosphine represented by the general formula (4) or (5). However, it is not necessary that the palladium-phosphine complex compound takes the above forms represented by the general formulae (10) and (11), and therefore the palladium-phosphine complex compound may be recovered in other and different forms. Such palladium-phosphine complex compound can be dissolved in many kinds of organic solvents and are stable in air.

In case that the aromatic compound represented by the general formula (2) is 3,5-bis(trifluoromethyl) bromobenzene, palladium-phosphine complex compound in which Ar is 3,5-bis(trifluoromethyl) group can be readily recovered. Examples of the palladium-phosphine complex compound are [3,5-bis(trifluoromethyl)benzoate] 3',5'-bis (trifluoromethyl) phenylbis(triphenylphosphine) palladium (II), and bromo[3,5-bis(trifluoromethyl) phenyl] bis (triphenylphosphine) palladium (II) can be readily recovered.

Palladium present in the reaction mixture or liquid is dissolved together with benzamides (products) in the solvent, and therefore it is required to separate the products, for which any separation method is usable. In view of an intention of the present invention, it is sufficient to remove the products and the necessarily produced by-products from the reaction system. It is not necessary to completely remove the products and the by-products; however, it is preferable to remove them as much as possible, from the viewpoint of obtaining a high throughput. For example, recovering the products and the by-products can be accomplished by using the difference in solubility of benzamides and palladium-phosphine complex compound relative to an organic solvent. Specifically, benzamides and palladium-phosphine complex compound which are taken out as water-insoluble matters from the reaction liquid are brought into contact with the organic solvent thereby extracting palladium-phosphine complex compound into the organic solvent. Then, the organic solvent is removed, for example, by distillation. Examples of such organic solvent are benzene, toluene, xylene, ethylbenzene, mesitylene. At least two of the above-listed solvents may be used upon being mixed. Additionally, hydrocarbon solvent such as pentane, hexane, heptane and the like; ester solvent such as ethyl acetate, butyl acetate and the like; and other general purpose solvents can be used as a part of the above solvent to be used for the purpose of removing the products and the by-products.

The operation for recovering the palladium-phosphine complex compound is made at a temperature ranging from 0 to 100° C. During the recovering operation, it may be made to cool the reaction liquid in accordance with kinds of the solvent in order to adjust the solubility; however, it is sufficient to carry out the recovering operation at ordinary or room temperature without making heating or cooling the reaction liquid.

The recovered palladium-phosphine complex compound can be purified by using a known method such as recrystallization. However, such purification is not particularly required for the recovered palladium-phosphine complex compound in the production method of the present invention.

At the fifth step (e), the palladium-phosphine complex compound obtained at the fourth step (d) is used as a part or whole of palladium and phosphine required for reaction like that the at first step (a).

The following examples are included merely to aid in the understanding of the invention, and variations may be made on the examples by one skilled in the art without departing from the spirit and scope of the invention. It will be understood that "pressure" used in the examples is indicated as gage pressure.

EXAMPLE 6

A 1000-ml autoclave made of stainless steel was charged with 400 g of 3,5-bis(trifluoromethy)bromobenzene, 227 ml of tetrahydrofuran, 1.53 g of palladium acetate, 5.37 g of triphenylphosphine, and 371 g of 25% ammonia water. Stirring for the content of the autoclave was started, upon which nitrogen gas displacement for the autoclave was made. Thereafter, the initial pressure of carbon monoxide gas was set at 3 kg/cm$^2$, and then heating for the autoclave was started. After lapse of 1 hour, the inside temperature of the autoclave reached 100° C., at which the inside pressure of the autoclave was adjusted at 10 kg/cm$^2$ upon introduction of carbon monoxide under pressure. During reaction, the inside temperature and pressure were respectively kept at 100° C. and 10 kg/cm$^2$. After lapse of 11 hours, the autoclave was cooled, and the gas inside the autoclave was purged. A reaction mixture or liquid was taken out into a separatory funnel, in which the reaction liquid was separated into two layers. One (organic layer) of the two layers was sampled. A separately prepared 2000-ml flask provided with a stirrer was charged with 700 ml of water and heated at 80 to 85° C. in an oil bath. At this time, the above sampled organic layer was added dropwise into the flask. When distillation of tetrahydrofuran had been completed, heating for the flask was stopped so as to cool the content of the flask to room temperature. Crystals formed in the cooled flask was subjected to a suction filtration, and thereafter rinsed with 900 ml of cool water and then rinsed with 250 ml of toluene two times to obtain a toluene-rinsed solution. As a result, 241.3 g of 3,5-bis(trifluoromethyl)benzamide was obtained. 3,5-bis(trifluoromethyl)benzamide had a melting point ranging from 160 to 162° C.

EXAMPLE 7

The toluene-rinsed solution in an amount of 500 ml, obtained in Example 6 was dried over magnesium sulfate anhydride and filtered to remove the magnesium sulfate. A filtrate was condensed by an evaporator thereby obtaining a residue. The residue was purified by a silica gel column chromatography using development solvent of n-hexane/ ethyl acetate=7/3 (v/v). As a result, 6.0 g of colorless crystals was obtained. The crystals were [3,5-bis(trifluoromethyl) benzoate] 3',5'-bis(trifluoromethyl) phenylbis (triphenylphosphine) palladium (II) (palladium complex compound) which was confirmed with the following data:

Melting point: 168–170° C. (decomp.); IR (KBr:cm$^{-1}$): 3060, 2926, 1637, 1437, 1321, 1277, 1173, 1127, 748, 697,518;

$^1$H-NMR (reference material: TMS, solvent: CDCl$_3$): δ ppm 6.97(s, 1H), 7.09 (s, 2H), 7.20–7.32 (m, 18H), 7.40–7.50 (m, 12H), 7.53 (s, 2H), 7.62(s, 1H); $^{31}$P-NMR (standard substance: 85% H$_3$PO$_4$, solvent: CDCl$_3$): δ ppm 25.73(s).

EXAMPLE 8

A 500-ml autoclave made of stainless steel was charged with 200 g of 3,5-bis(trifluoromethy)bromobenzene, 120 ml of tetrahydrofuran, 3.74 g of the palladium complex compound recovered in Example 7, and 185 g of 25% ammonia water. Stirring for the content of the autoclave was started, upon which nitrogen gas displacement for the autoclave was made. Thereafter, the initial pressure of carbon monoxide gas was set at 1 kg/cm$^2$, and then heating for the autoclave was started. After lapse of 1 hour, the inside temperature of the autoclave reached 100° C., at which the inside pressure of the autoclave was adjusted at 10 kg/cm$^2$ upon introduction of carbon monoxide under pressure. During reaction, the inside temperature and pressure were respectively kept at 100° C. and 10 kg/cm$^2$.

After lapse of 8 hours, the autoclave was cooled, and the gas inside the autoclave was purged. A reaction mixture or liquid was taken out into a separatory funnel, in which the reaction liquid was separated into two layers. One (organic layer) of the two layers was sampled. A separately prepared 2000-ml flask provided with a stirrer was charged with 400 ml of water and heated at 80 to 85° C. in an oil bath. At this time, the above sampled organic layer was added dropwise into the flask. When distillation of tetrahydrofuran had been completed, heating for the flask was stopped so as to cool the content of the flask to room temperature. Crystals formed in the cooled flask was subjected to a suction filtration, and thereafter rinsed with 500 ml of cool water and then rinsed with 300 nil of toluene two times. As a result, 124 g of 3,5-bis(trifluoromethyl)benzanide was obtained.

What is claimed is:

1. A method of producing benzamides represented by the following general formula (1):

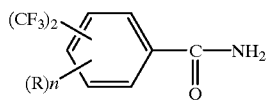
(1)

where R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or a alkoxycarbonyl group having 2 to 5 carbon atoms; and n is 0 or an integer ranging from 1 to 3, said method comprising the step:
allowing an aromatic compound represented by the following general formula (2) to react with carbon monoxide and ammonia in the presence of a metal of the group VIII of the periodic table and phosphine:

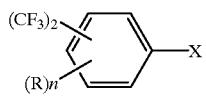
(2)

where X is halogen (fluorine, chlorine, bromine or iodine), trifluoromethanesulfonate group, alkylsulfonate group having 1 to 4 carbon atoms, or substituted or unsubstituted arylsulfonate group; R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or alkoxycarbonyl group having 2 to 5 carbon atoms; and n is 0 or an integer ranging from 1 to 3.

2. A method as claimed in claim 1, wherein said X is halogen (fluorine, chlorine, bromine or iodine).

3. A method as claimed in claim 1, wherein X is bromine or iodine, and R is fluorine, chlorine, bromine or iodine.

4. A method as claimed in claim 1, wherein said aromatic compound represented by the general formula (2) is hologeno(trifluoromethyl) benzene represented by the following general formula (3):

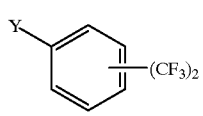
(3)

where Y is bromine or iodine.

5. A method as claimed in claim 1, wherein said aromatic compound represented by the general formula (2) is 3,5-bis(trifluoromethyl)bromobenzene, 3,5-bis(trifluoromethyl)iodobenzene, or 2-chloro-3,5-bis(trifluoromethyl)bromobenzene.

6. A method as claimed in claim 1, wherein said metal of the group VIII of the periodic table is at least one metal selected from the group consisting of iron, cobalt, palladium, platinum, rhodium, ruthenium, iridium, and osmium.

7. A method as claimed in claim 1, wherein said metal of the group VIII of the periodic table is palladium.

8. A method as claimed in claim 1, wherein said phosphine is first phosphine represented by the general formula (4):

where $R^1$ independently represents lower alkyl group, phenyl group or phenyl group substituted with lower alkyl group; or second phosphine represented by the general formula (5):

where $R^1$ is defined as above; and Q is a bivalent group.

9. A method as claimed in claim 1, wherein said phosphine is triphenylphosphine, 1,3-bis(diphenylphosphino) propane, or 1,4-bis(diphenylphosphino) butane.

10. A method as claimed in claim 1, wherein said metal of the group VIII of the periodic table and said phosphine are used in any combination of metal salt, phosphines, and metal phosphine complex.

11. A method as claimed in claim 1, wherein at least one of water and solvent is present in the reaction system in which said aromatic compound is allowed to react.

12. A method as claimed in claim 1, wherein water is present in the reaction system in which said aromatic compound is allowed to react.

13. 2-chloro-3,5-bis(trifluoromethyl) benzamide.

14. A method of producing benzamides, comprising the following steps:
(a) allowing an aromatic compound represented by the following general formula (2) to react with carbon monoxide and ammonia in the presence of palladium and phosphine in a reaction system:

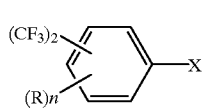
(2)

where X is halogen (fluorine, chlorine, bromine or iodine), trifluoromethanesulfonate group, alkylsulfonate group having 1 to 4 carbon atoms, or substituted or unsubstituted arylsulfonate group; R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or a alkoxycarbonyl group having 2 to 5 carbon atoms; and n is 0 or an integer ranging from 1 to 3, (b) separating at least benzamide represented by the following general formula (1):

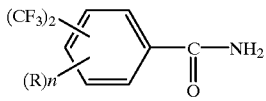

(1)

where R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or a alkoxycarbonyl group having 2 to 5 carbon atoms; and n is 0 or an integer ranging from 1 to 3; and (c) adding said aromatic compound represented by the general formula (2), ammonia and carbon monoxide into the reaction system from which at least said benzamide is separated, so as to accomplish reaction in the reaction system.

15. A method of producing benzamides, comprising the following steps:

(a) allowing an aromatic compound represented by the following general formula (2) to react with carbon monoxide and ammonia in the presence of palladium and phosphine in a reaction system:

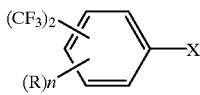

(2)

where X is halogen (fluorine, chlorine, bromine or iodine), trifluoromethanesulfonate group, alkylsulfonate group having 1 to 4 carbon atoms, or substituted or unsubstituted arylsulfonate group; R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or a alkoxycarbonyl group having 2 to 5 carbon atoms; and n is 0 or an integer ranging from 1 to 3, (b) separating at least benzamide represented by the following general formula (1):

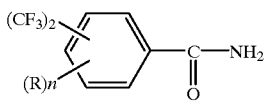

(1)

where R is trifluoromethyl group, trifluoromethyloxy group, halogen (fluorine, chlorine, bromine or iodine), nitro group, acetyl group, cyano group, alkyl group having 1 to 4 carbon atoms, alkoxy group having 1 to 4 carbon atoms, or a alkoxycarbonyl group having 2 to 5 carbon atoms; and n is 0 or an integer ranging from 1 to 3;

(d) recovering palladium-phosphine complex compound from the reaction system; and (e) using the palladium-phosphine complex compound recovered in the step (d) as a catalyst.

16. A method as claimed in claim 14, wherein said phosphine is first phosphine represented by the general formula (4):

$P(R^1)_3$ (4)

where $R^1$ independently represents lower alkyl group, phenyl group or phenyl group substituted with lower alkyl group; or second phosphine represented by the following general formula (5):

$(R^1)_2P—Q—P(R^1)_2$ (9)

where $R^1$ independently represents lower alkyl group, phenyl group, phenyl group substituted with lower alkyl group; and Q is a bivalent group.

17. A method as claimed in claim 14, wherein said phosphine is triphenylphosphine, 1,3-bis(diphenylphosphino)propane, or 1,4-(diphenylphosphino)butane.

18. A method as claimed in claim 15, wherein said palladium-phosphine complex compound is represented by the following general formula (10):

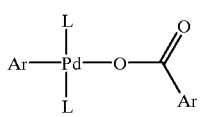

(10)

where Ar is aryl group; and L is first phosphine represented by the general formula (4):

$P(R^1)_3$ (4)

where $R^1$ independently represents lower alkyl group, phenyl group or phenyl group substituted with lower alkyl group; or second phosphine represented by the general formula (5):

$(R^1)_2P—Q—P(R^1)_2$ (5)

where $R^1$ is defined as above; and Q is a bivalent group; or the following general formula (11):

$Ar—PdL_2X$ (11)

where Ar is aryl group; X is halogen (fluorine, chlorine, bromine or iodine), trifluoromethanesulfonate group, alkylsulfonate group having 1 to 4 carbon atoms, or substituted or unsubstituted arylsulfonate group; and L is defined as above.

19. A method as claimed in claim 15, wherein said palladium and said phosphine are used in any combination of palladium salt, phosphines, palladium complex, and said palladium-phosphine complex compound recovered in the step (d).

20. A method as claimed in claim 18, wherein Ar in said palladium-phosphine complex compound represented by the general formula (10) is bis(trifluoromethyl phenyl group.

21. A method as claimed in claim 20, wherein L in said palladium-phosphine complex compound represented by the general formula (10) is triphenylphosphine, o-tolylphosphine, m-tolylphosphine, or p-tolylphosphine.

* * * * *